(12) United States Patent
Ogasawara

(10) Patent No.: US 7,022,079 B2
(45) Date of Patent: Apr. 4, 2006

(54) ULTRASONIC DIAGNOSTIC APPARATUS

(75) Inventor: Yoichi Ogasawara, Nasu-gun (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 10/782,976

(22) Filed: Feb. 23, 2004

(65) Prior Publication Data
US 2004/0159155 A1 Aug. 19, 2004

Related U.S. Application Data

(63) Continuation of application No. PCT/JP02/08475, filed on Aug. 22, 2002.

(30) Foreign Application Priority Data

Aug. 22, 2001 (JP) ............................. 2001-251766

(51) Int. Cl.
*A61B 8/00* (2006.01)

(52) U.S. Cl. .................................. 600/458

(58) Field of Classification Search ................ 600/437, 600/438, 443, 447, 458, 504, 507
See application file for complete search history.

(56) References Cited

U.S. PATENT DOCUMENTS

| 5,860,931 | A | * | 1/1999 | Chandler | .................... | 600/458 |
| 5,935,069 | A | * | 8/1999 | Chandler et al. | ........... | 600/443 |
| 6,149,597 | A | | 11/2000 | Kamiyama | | |
| 6,315,730 | B1 | * | 11/2001 | Hoff et al. | ................... | 600/458 |

FOREIGN PATENT DOCUMENTS

| JP | 11-155858 | 6/1999 |
| JP | 2001-70304 | 3/2001 |
| WO | WO 98/45733 | 10/1998 |
| WO | WO 00/30541 | 6/2000 |

* cited by examiner

*Primary Examiner*—Francis J. Jaworski
(74) *Attorney, Agent, or Firm*—Oblon, Spivak, McClelland, Maier & Neustadt, P.C.

(57) ABSTRACT

With respect to a scanning plane of a subject having been injected with a contrast agent, an ultrasound transmission section 6 transmits for a plurality of times an ultrasonic pulse of such an intensity capable of collapsing the contrast agent. An ultrasound reception section 5 receives an echo signal cluster from the subject based on the ultrasonic pulses, and generates a plurality of RF data items through addition of the echo signal cluster using an adder 5C. Based on the plurality of RF data items, a TIC/MTT measurement section 25 measures a time intensity curve (TIC), and then measures a mean transit time (MTT) of the blood flow based on the time intensity curve for display on a display section 21.

10 Claims, 13 Drawing Sheets

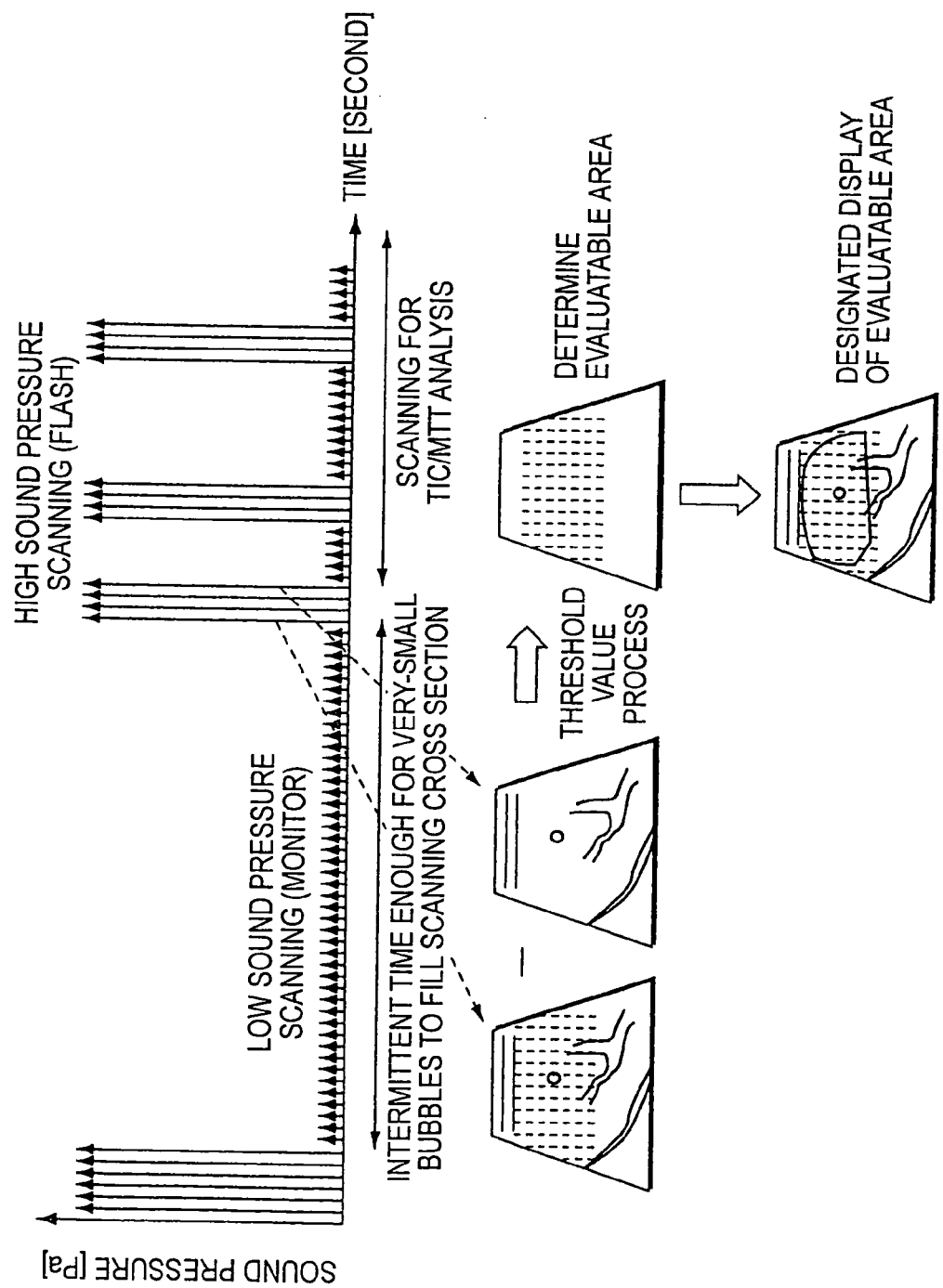

ULTRASONIC DIAGNOSTIC APPARATUS

CROSS-REFERENCE TO RELATED APPLICATIONS

This is a Continuation Application of PCT Application Ser. No. PCT/JP02/08475, filed Aug. 22, 2002, which was not published under PCT Article 21(2) in English.

This application is based upon and claims the benefit of priority from prior Japanese Patent Application No. 2001-251766, filed Aug. 22, 2001, the entire contents of which are incorporated herein by reference.

BACKGROUND OF THE INVENTION

1. Field of the Invention

The present invention relates to an ultrasonic diagnostic apparatus capable of quantitatively assessing blood flow behaviors using a contrast agent for ultrasound.

2. Description of the Related Art

An ultrasonic diagnostic apparatus is medical image equipment with which tomographic images of soft tissues beneath the body surface are derived from a living body in a noninvasive manner by the ultrasonic pulse echo method, and has been popular in the Departments relating to hearts, abdominal regions, and urinary, and the Department of obstetrics and gynecology. This ultrasonic diagnostic apparatus is, characteristically, smaller in size and lower in price than other types of medical image equipment (e.g., X-ray diagnostic equipment, X-ray CT equipment, MRI diagnostic equipment, nuclear medicine diagnostic equipment), capable of real time display, capable of offering a high level of safety without X-ray exposure, capable of blood flow imaging, and the like. Recently, the contrast echo has become popular with techniques in which more detailed diagnostic images are derived by increasing echo effects of ultrasound thanks to the contrast agent that has been injected into a subject. For example, with cardiac and abdominal organ examinations utilizing the contrast echo, the contrast agent for ultrasound is injected from a low-invasive vein to collect ultrasonic echo signals having intensified by thus injected contrast agent. Generating diagnostic images based on such echo signals allows estimation of the blood flow behaviors in a more detailed manner.

As the imaging technique is established in image diagnosis, the quantitative assessment using the contrast agent has become popular for study. The functional diagnosis through quantitative assessment has become advanced especially in the field of nuclear medicine and others in which pharmaceutical drug study utilizing metabolic functions is active. Exemplarily in a circulatory system, myocardial functional assessments are made utilizing a time intensity curve (TIC: Time Intensity Curve) as a result of plotting time-varying intensity information. Resultantly derived thereby are the time in the contraction phase taken to reach the maximum contraction speed from the last period of expansion, the maximum contraction speed, and the like. Needless to say to the ultrasonic diagnostic apparatus, such a TIC is applicable also to X-ray, X-ray CT, and MRI, all of which are operable using the contrast agent.

As another type of quantitative assessment using the contrast agent, known is a technique of calculating a mean transit time (MTT: Mean Transit Time: in the below, referred to as "MTT") of the blood flow using the TIC. Such an MTT allows assessment of the blood flow behaviors in organs, and measurement of the flow volume in a quantitative manner.

Also in the ultrasonic diagnostic apparatus, quantitative analysis is becoming possible, such as TIC measurement using the contrast agent, and MTT analysis based on the TIC.

FIG. 1 is a diagram for illustrating the MTT. In FIG. 1, in a case of administering the contrast agent on a continual basis, the MTT will be the value to be derived in the following manner. That is, first calculated is an area S enclosed by a saturation value and a TIC between the administration starting time of the contrast agent and the time of reaching the saturation value, and the result is then normalized by the saturation value. Herein, the area calculation and the normalization may be executed in the reverse order, and if this is the case, the TIC may be first normalized by the saturation value to calculate the 5 area.

The issue here is that, the contrast agent used for ultrasonic diagnosis is composed of very-small bubbles, and has such a peculiar physical property that the contrast agent itself may be collapsed and vanished. Thus, simply applying the technique so far used with the MTT in other diagnostic apparatuses cannot realize the quantitative assessment with assured objectivity and accuracy. At present, the MTT in ultrasonic diagnosis is under study quite actively. For example, as to such problems as effects of bioattenuation in any examination using the contrast agent for ultrasound, and varying concentrations of the contrast agent whenever it is a generally known solution therefore is normalization by saturation values.

However, the following problems are not yet solved to put the MTT into practical use in the ultrasonic diagnostic apparatus, for example.

The first problem is the varying MTTs due to uneven beam shapes. To be specific, generally, if the beam shapes are uneven in the depth direction, assessing any two point regions different in beam shape will result in varying volumes available for the very-small bubbles to collapse and vanish. If this is the case, even if a TIC is plotted for regions different in beam shape with respect to organs having the same level of blood flow behaviors without depending on the depth, for example, the resulting saturation values, i.e., maximum values, may still vary. Thus, the normalized TICs show no coincidence, resulting in varying MTTs depending on the depth.

Moreover, using the contrast agent bubbles requires the longer measurement time compared with TIC measurement with other types of medical equipment. In detail, responding to ultrasound exposure, very-small bubbles in thus exposed plane are collapsed and vanished. Therefore, for data acquisition within a sample time required for plotting a TIC, there requires another ultrasound exposure with a wait until the very-small bubbles again fill the same exposed plane. With TIC measurement in diagnosis utilizing flash echo imaging, there requires a data cluster corresponding to each intermittent time interval. Further, if temporal samplings are increased in number to plot a TIC, the cross section under study has to be maintained longer by the time thus increased corresponding to the time interval between the temporal samplings. In an exemplary case where a TIC covering 20 [seconds] is plotted with the temporal samplings of every 1 [second], it simply takes 20 [seconds] with X-ray enhanced and X-ray enhanced CT. On the other hand, in a case of using the contrast agent for ultrasound, it takes $$1+2+3+\ldots+18+19+20=210 \text{ [seconds]}=3.5\text{[minutes]}$$

This is because every time scanning is done, the very-small bubbles being the contrast agent collapse and vanish, and thus resetting is required. During that time, the operator thus has to maintain the cross section. If so, however, it is difficult to securely keep the scanning cross section at the same position. There is a possibility of checking the cross section by performing so-called monitor mode scanning with low sound pressure level not to collapse nor vanish the very-small bubbles, however, this requires to retain the probe for a long absolute time. Still more the long-time administration of the contrast agent for ultrasound, and the resulting long-time examination will be disadvantageous for doctors, operators, and patients.

Furthermore, there may be a case where the very-small bubbles are not fully collapsed or vanished if the contrast agent is of a type hardly collaping or vanishing, if the contrast agent is high in concentration, or if the transmission sound pressure is low. As such, if the bubbles are not fully collapsed or vanished, it results in the following drawbacks.

Firstly, the resulting MTTs will vary depending on the depth. This is because, even if the blood flow rate of the blood flow is constant without depending on the depth in any organ under study, when the selection position of ROI (Region of Interest) changes in the depth direction, the ratio of the very-small bubbles collapsing and vanishing also changes depending on the depth. This is because the transmission ultrasound is attenuated due to reflection and scattering in the process of passing over the very-small bubbles and collapsing those, or in the process of passing through the living body. Secondly, if the very-small bubbles are remained, it means that a signal derived by the next intermittent transmission resultantly includes an offset of the remaining bubbles. Thus, the flow volume of the very-small bubbles, i.e., blood flow rate, cannot be correctly obtained, thereby failing in deriving correct MTTs after all. Thirdly, as described in the foregoing, due to attenuation of the transmission ultrasound or attenuation of the reflected ultrasound, nearly no signal will be returned if the depth reaches at a certain point. Thus, due to a so-called shadowing phenomenon in which shadows are cast on images, there exists regions being not accessible.

The present invention is proposed in consideration of the above circumstances, and an object thereof is to provide an ultrasonic diagnostic apparatus with which effects caused by the depth can be reduced, and MTTs can be derived with assured accuracy and with high reproducibility through short-time scanning.

BRIEF SUMMARY OF THE INVENTION

To achieve the above object, the present invention takes the following means.

A first viewpoint of the present invention is directed to an ultrasonic diagnostic apparatus, including: an ultrasonic probe for transmitting ultrasound to a subject having been injected with a contrast agent, and receiving ultrasonic echo from the subject; a driving signal generator for generating a driving signal for driving the ultrasonic probe; a control unit for performing scanning for a plurality of times with ultrasound of such a high intensity that the contrast agent is collapsed at a time-varying time interval after the contrast agent is injected, and controlling the driving signal generator based on a scan sequence in which the time interval after the scanning performed for the initial time is set to be 5 seconds or shorter; and a processor for plotting a time-varying concentration graph of the contrast agent based on the ultrasonic echo.

A second viewpoint of the present invention is directed to an ultrasonic diagnostic apparatus, including: an ultrasonic probe for transmitting ultrasound to a subject having been injected with a contrast agent, and receiving ultrasonic echo from the subject; a driving signal generator for generating a driving signal for driving the ultrasonic probe; a control unit for controlling the driving signal generator based on a scan sequence in which scanning is performed for a plurality of times with a constant time interval after the contrast agent is injected; and a processor for plotting a time-varying concentration graph of the contrast agent based on a plurality of cumulative values or average values of the ultrasonic echo as a result of the scanning performed for the plurality of times.

A third viewpoint of the present invention is directed to an ultrasonic diagnostic apparatus, including: an ultrasonic probe for transmitting ultrasound to a subject having been injected with a contrast agent, and receiving ultrasonic echo from the subject; a driving signal generator for generating a driving signal for driving the ultrasonic probe; a control unit for controlling the driving signal generator based on a predetermined scan sequence for plotting a time-varying concentration graph of the contrast agent; a signal processor for applying a detection process and a logarithmic transformation process to the ultrasonic echo; an image generator for generating an ultrasonic image based on an output of the signal processor; an antilogarithmic transformation unit for applying an antilogarithmic transformation process to at least an output signal coming from either of the signal processor or the image generator; and a processor for plotting a time-varying graph based on the output signal coming from the antilogarithmic transformation unit.

A fourth viewpoint of the present invention is directed to an ultrasonic diagnostic apparatus, including: an ultrasonic probe for transmitting ultrasound to a subject having been injected with a contrast agent, and receiving ultrasonic echo from the subject; a driving signal generator for generating a driving signal for driving the ultrasonic probe; a control unit for controlling the driving signal generator based on a predetermined scan sequence for plotting a time-varying concentration graph of the contrast agent; a signal generator for generating a first signal as a result of a detection process and a logarithmic transformation process applied with respect to the ultrasonic echo, and a second signal as a result of the detection process applied with respect to the ultrasonic echo; an image generator for generating an ultrasonic image based on the first signal; and a measurement processor for plotting the time-varying graph based on the second signal.

A fifth viewpoint of the present invention is directed to an ultrasonic diagnostic apparatus, including: an ultrasonic probe for transmitting ultrasound to a subject having been injected with a contrast agent, and receiving ultrasonic echo from the subject; a driving signal generator for generating a driving signal for driving the ultrasonic probe; a control unit for controlling the driving signal generator based on a predetermined scan sequence for deriving a time-varying concentration of the contrast agent; an image generator for generating an ultrasonic image based on the ultrasonic echo; and a measurement processor for plotting a time-varying concentration graph of the contrast agent based on the ultrasonic echo, and for compensating a mean transit time of a blood flow derived from the time-varying graph depending on a measurement position depth.

A sixth viewpoint of the present invention is directed to an ultrasonic diagnostic apparatus, including: an ultrasonic probe for transmitting ultrasound to a subject having been injected with a contrast agent, and receiving ultrasonic echo from the subject; a driving signal generator for generating a driving signal for driving the ultrasonic probe; a control unit for controlling the driving signal generator based on a predetermined scan sequence for plotting a time-varying concentration graph of the contrast agent; an image generator for generating an ultrasonic image based on the ultrasonic echo; and a measurement processor for plotting the time-varying concentration graph of the contrast agent based on the ultrasonic echo, and for compensating the time-varying graph depending on a measurement position depth.

According to such structures, realized is an ultrasonic diagnostic apparatus with which MTTs can be derived with assured accuracy and with high reproducibility through short-time scanning.

BRIEF DESCRIPTION OF THE SEVERAL VIEWS OF THE DRAWING

FIG. 6A is a schematic view of a beam profile in the slice-thickness direction. FIG. 6B is a diagram showing TICs (before and after normalization) as a result of measurement using echo signals coming from positions A and B, respectively, in FIG. 6A. FIG. 6C is a diagram showing MTTs derived by FIG. 6B.

FIG. 7 is a conceptual diagram for illustrating an area that is measurable by the TIC or MTT.

BEST MODE FOR CARRYING OUT THE INVENTION

Figure 1:
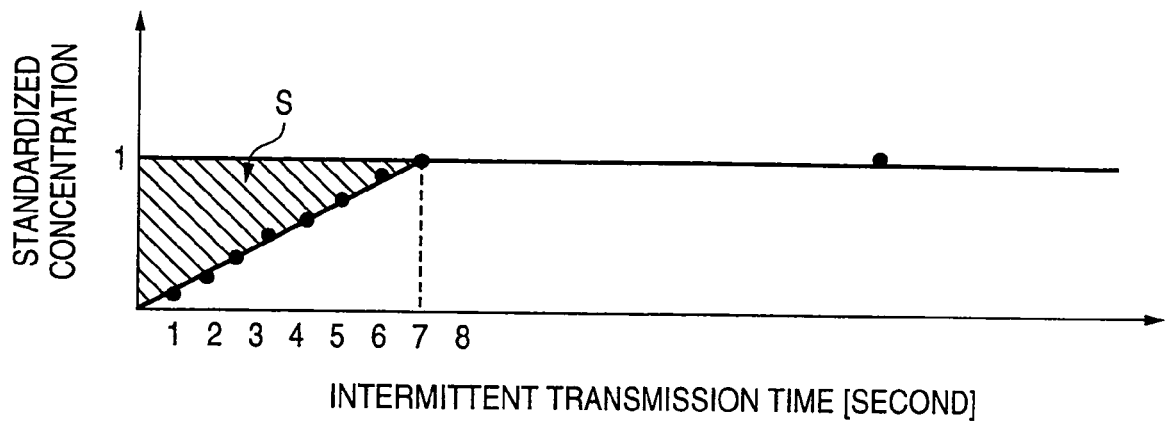
FIG. 1 is a diagram for illustrating an MTT.

In the below, first to fifth embodiments of the present invention are described by referring to the accompanying drawings. Note that, in the following description, any component sharing almost the same function and structure will be provided with the same reference numeral, and will be described again if necessary.

(First Embodiment)

Figure 2:
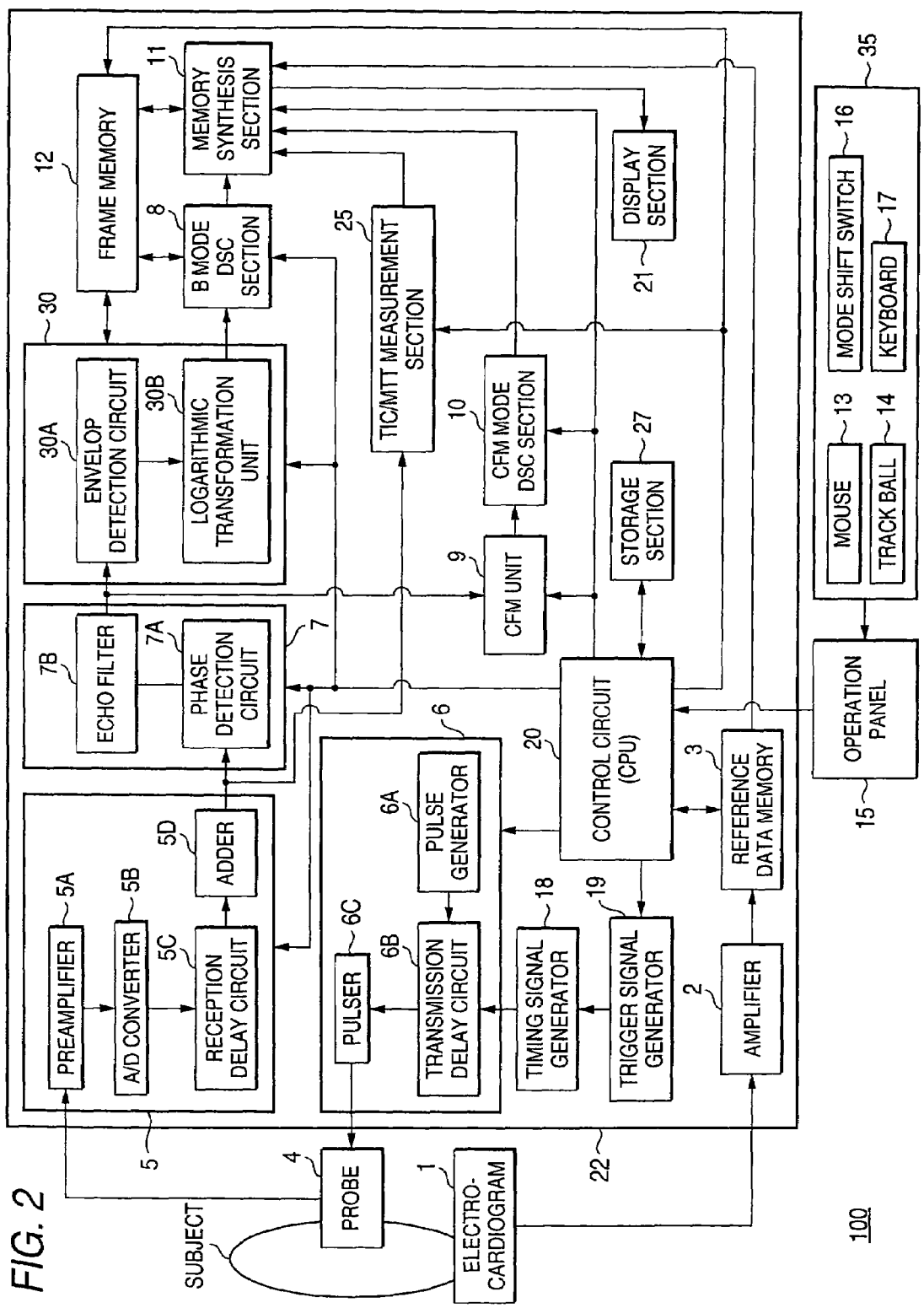
FIG. 2 is a block diagram showing the structure of an ultrasonic diagnostic apparatus 100 of a present embodiment.

First of all, described is the structure of an ultrasonic diagnostic apparatus 100 of a first embodiment by referring to FIG. 2. The ultrasonic diagnostic apparatus 100 of the present embodiment is the one performing TIC/MTT measurement utilizing RF data (data after phase addition) as will be described later.

FIG. 2 is a block diagram showing the structure of the ultrasonic diagnostic apparatus 100. As shown in FIG. 2, the present ultrasonic diagnostic apparatus 100 is structured by an electrocardiogram (ECG) 1, an ultrasonic probe 4, an apparatus body 22, an operation panel 15, and an input unit 35. In the below, each of those components will be described.

The electrocardiogram (ECG: ElectroCardioGram) 1 measures a graph having recorded the time-varying electrical phenomena of a subject's heart, i.e., electrocardiogram. Electrocardiogram waveform signals detected by the electrocardiogram 1 are forwarded to reference data memory 3 via an amplifier 2, and if required, forwarded to a display section 21 via a memory synthesis section 11 to be displayed as electrocardiogram waveforms.

The ultrasonic probe 4 has a piezoelectric transducer as an electroacoustic reversible transducer such as piezoelectric ceramics. Such a piezoelectric transducer is plurally arranged in parallel to be equipped at the tip of the probe 4.

The operation panel 15 is connected to an apparatus body 22, and is provided with the input unit 35 (mouse 13, trackball 14, mode shift switch 16, keyboard 17, and others) for setting Region of Interest (ROI) to capture various instructions, commands, and information coming from an operator into the apparatus body 22.

The apparatus body 22 is provided with: the amplifier 2; the reference data memory 3; an ultrasound reception section 5; an ultrasound transmission section 6; a receiver section 7; a B mode DSC section 8; a CFM unit 9; a CFM mode DSC section 10; the memory synthesis section 11; frame memory 12; a timing signal generator 18; a trigger signal generator 19; a control circuit (CPU) 20; the display section 21; a TIC/MTT measurement section 25; a storage section 27; and a B mode unit 30.

The ultrasound transmission section 6 is provided with a pulse generator 6A, a transmission delay circuit 6B, and a pulser 6C, and is connected to the probe 4.

The pulse generator 6A repeatedly generates a rate pulse at a rate frequency frHz (period: 1/fr second) of 5 kHz, for example. This rate pulse is split into the number of channels, and then forwarded to the transmission delay circuit 6B. To the respective rate pulses, the transmission delay circuit 6B provides the delay time needed to apply beam focusing with respect to the ultrasound and to determine the transmission directivity. Herein, to the transmission delay circuit 6B, a trigger coming from the trigger signal generator 19 is supplied as a timing signal via the timing signal generator 18. In the pulser 6C, voltage pulse application is made on a channel basis to the probe 4 at the timing of a rate pulse received from the transmission delay circuit 6B. Responding to this pulse, the piezoelectric transducer of the probe 4 is driven, and ultrasonic beams are generated for transmission to the subject.

Herein, responding to the selection of MTT mode using the mode shift switch 16, scanning is started by the scan sequence that has been programmed in advance with interframe transmission intervals.

The reflected waves transmitted as above and reflected by discontinuously-arranged planes of acoustic impedance in the subject are received by the probe. Thus received reflected waves are output as echo signals on a channel basis, and captured into the ultrasound reception section 5.

The ultrasound reception section 5 is provided with a preamplifier 5A, an A/D converter 5B, a reception delay circuit 5C, and an adder 5D. The preamplifer 5A amplifies, on a channel basis, the echo signals thus captured into the ultrasound reception section 5 via the probe 4. Thus amplified echo signals are provided with the delay time needed to determine the reception directivity by the reception delay circuit 5C, and then subjected to addition in the adder 5D. Such an addition resultantly enhances the reflection components from the direction corresponding to the reception directivity of the echo signals. By the reception directivity and the directivity at the time of transmission, the comprehensive directivity for ultrasonic transmission and reception is determined. This comprehensive directivity is generally referred to scanning lines. The echo signals having been subjected to such a series of processes are forwarded from the ultrasound reception section 5 to the receiver section 7.

The receiver section 7 goes through phase detection to extract signals of any desired frequency band using an echo filter. Herein, thus extracted data is referred to as IQ data, and the IQ data is forwarded from the receiver section 7 to the B mode unit 30 or a color flow mapping (CFM) unit 9.

The B mode unit 30 is structured by an envelop detection circuit 30A and a logarithmic transformation unit 30B. The envelop detection circuit 30A detects any envelop of an output signal coming from the receiver section 7. The resulting data detected as such is referred to as B-mode detection data. The logarithmic transformation unit 30B applies a compression process to the B-mode detection data using logarithmic transformation. Note here that, in the following description, signals before such envelop detection and logarithmic transformation are referred to as IQ data, and data after such envelop detection and logarithmic transformation are referred to as B-mode raster data.

Although not shown, the color flow mapping (CFM) unit 9 is structured by a phase detection circuit, an analog/digital converter, an MTI filter, an autocorrelator, and an arithmetic unit. Thereby, the blood flow components are extracted by Doppler effect, and blood flow information such as average speed, variance, and power are derived for various points. The blood flow information is forwarded to the display section 21 via the CFM mode DSC section 10, and the memory synthesis section 11, and then color-displayed as an average speed image, a variance image, a power image, and a combination image thereof.

As a control nerve in the entire system, the control circuit (CPU) 20 applies control relating to the operation of the present ultrasonic diagnostic apparatus, especially control relating to ultrasonic image diagnosis by intermittent transmission, which will be described later.

The TIC/MTT measurement section 25 performs measurement of a TIC (Time Intensity Curve: time-intensity change curve) and an MTT (Mean Transit Time: mean transit time) based on the RF data and others having been subjected to phase addition by the adder 5D but not yet subjected to the process by the receiver section 7. The TIC/MTT measurement process to be executed by the TIC/MTT measurement 25 as such will be described later in detail.

Both the B-mode digital scan converter (DSC) section 8 and the CFM digital scan converter (DSC) section 10 convert a string of ultrasonic scanning line signals that have been input from the B-mode unit 30 into data of orthogonal coordinate system based on spatial information. At the time when data transmission is carried out from the memory synthesis section 11 to the display section 21, video format conversion is performed.

The memory synthesis section 11 synthesizes, into a frame, text information of various setting parameters, scales, or guidance images that will be described later, and others. Then, applied is the conversion process into a string of scanning line signals of general video format typified by televisions, and the like, and the result is output to the display section 21 as video signals.

On the display section 21, displayed as images are the morphological compromise and blood flow information in the living body. When the contrast agent is used, displayed on the display section 21 are intensity images and color images based on the spatial distribution of the contrast agent, that is, quantitative information volume as a result of deriving regions in which any blood flow or blood is observed. The frame memory 12 is provided for storage of digital data output of the memory synthesis section 11.

The storage section 27 is storage means for storing, on the basis of depth D, the acoustic fields V each indicating the spatial size against the sound pressure that can collapse and vanish the very-small bubbles. Herein, the value of acoustic field V is determined by measurement in advance or simulation while controlling the parameters of ultrasound to be irradiated from the probe 4 such as frequency, focus point, and MI value. The storage section 27 may be in any form as long as capable of storing electrical data, for provision, such as hard disks, FDs, CDs, or MDs. (TIC/MTT Measurement)

Described next is the TIC measurement process and the MTT measurement process to be executed by the present ultrasonic diagnostic apparatus. Herein, the TIC and MTT measurement processes are both executed by the TIC/MTT measurement section 25 under the control of the CPU 20.

Figure 3:
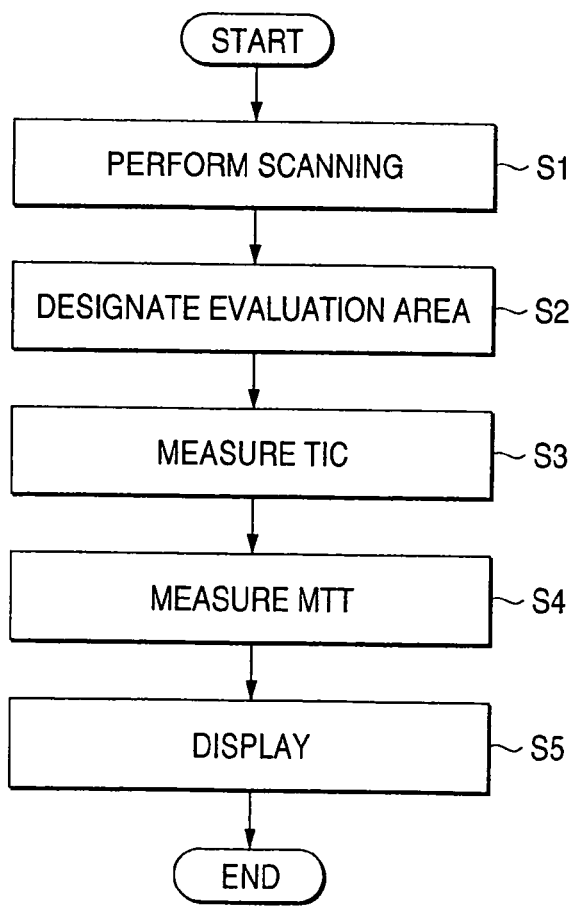
FIG. 3 is a flowchart showing the process procedure of TIC/MTT measurement to be executed by the ultrasonic diagnostic apparatus 100.
Figure 4:
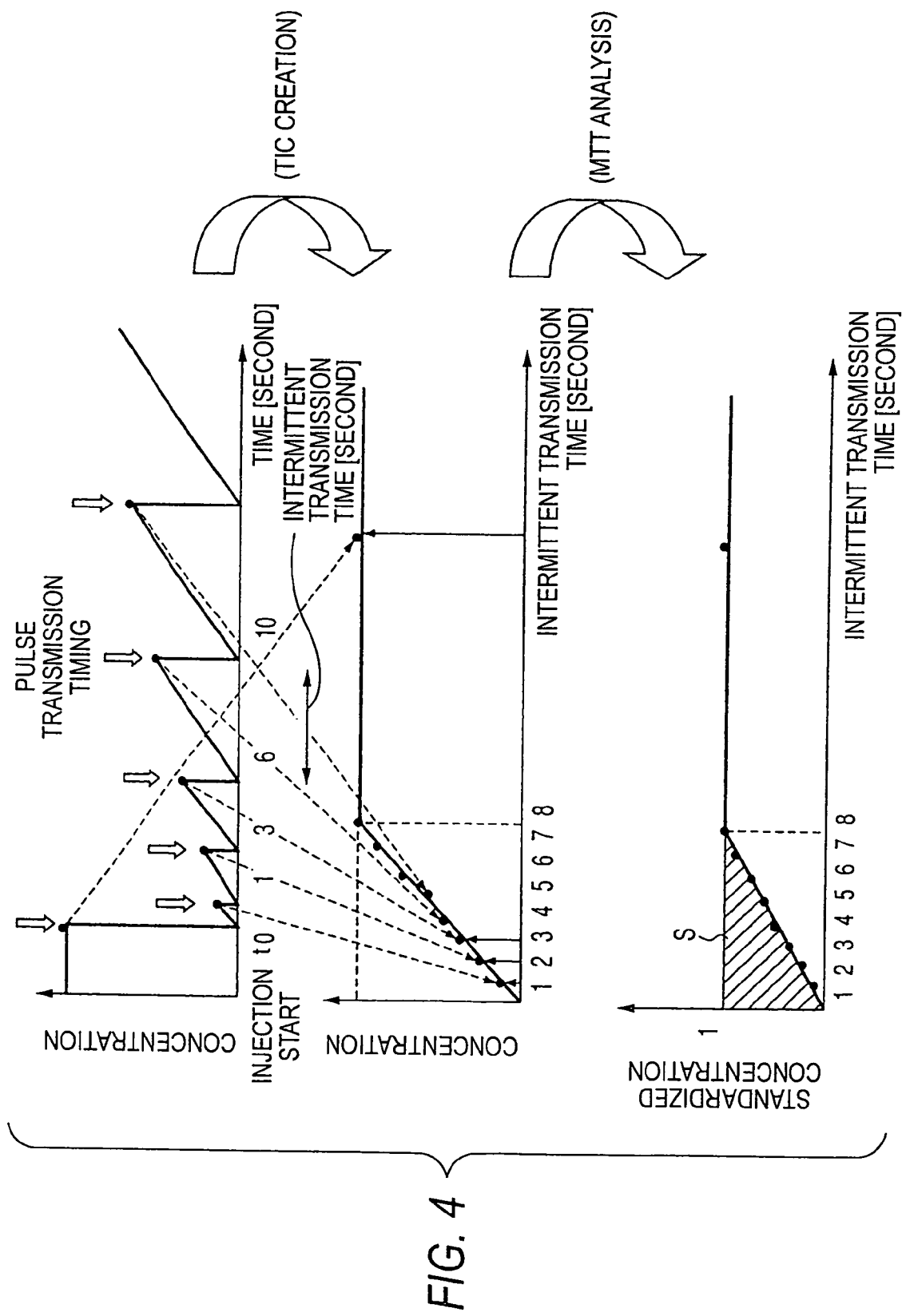
FIG. 4 is a conceptual diagram for illustrating the resulting TIC and MTT derived by the process of TIC/MTT measurement.

FIG. 3 is a flowchart showing the process procedure of the TIC/MTT measurement to be executed by the present ultrasonic diagnostic apparatus. FIG. 4 is a diagram for illustrating TICs and MTTs derived by the TIC and MTT measurement processes.

In FIG. 3, first, scanning is performed under the contrast echo (step S1).

Note here that the contrast agent currently in use for ultrasound is generally composed of very-small bubbles. Accordingly, it is collapsed or vanished if exposed to ultrasound for imaging, and thus continuous scanning is not appropriate thereto as is popular for any other medical image equipment. In the present ultrasonic diagnostic apparatus, scanning of step S1 is performed based on such a sequence as shown in the upper part of FIG. 4, for example.

(1) First, injection of the contrast agent is started. The contrast agent is gently injected into a vein on a measured amount basis (alternatively, bolus injection is a possibility, and in this case, wait until the contrast agent concentration becomes stable by blood flow circulation).

Next, the ultrasonic probe is placed at any position considered appropriate, and then after transmission and reception, the very-small bubbles in the observation area are collapsed for resetting. Alternatively, the very-small bubbles are collapsed for resetting while aiming at the blood vessel being a supply source from which the contrast agent is provided for the observation area (time t0 of FIG. 4). At this time, if the very-small bubbles are fully filled, the harmonic components derived at this time will be the maximum value of the receiving echo signal.

(3) As shown in FIG. 4, transmission is stopped (temporarily stopped) only for a desired time interval t0, and when the set time comes, transmission and reception is performed for a frame. In this manner, derived are the harmonic components from the very-small bubbles so far flown into. Such transmission and reception is performed for a plurality of times with respect to any one specific cross section. Herein, the ultrasound transmission with any desired time intervals as such is referred to as the intermittent transmission or flash echo (Flash Echo). With such intermittent transmission, to diagnose abdominal regions, for example, it is preferable to set the transmission temporary-stop period, which is after the scanning is performed for the first time, generally to 5 seconds or less, and preferably, to 3 seconds or less. In an exemplary case where the abdominal regions are diagnosed, this transmission temporary-stop period can be measured by the internal counter provided to the ultrasonic diagnostic apparatus 100, and if with circulatory organs, by the ECG 1.

According to such intermittent transmission, any organ to be diagnosed is exposed to the ultrasound after the contrast agent for ultrasound is fully filled therein to aggressively collapse and vanish the contrast agent. In such a manner, derived is a strong signal from the very-small bubbles. Here, scanning repeated for a plurality of times with respect to the same cross section is referred to as multishot. Such multishot can cancel the effects caused by the remaining very-small bubbles.

(4) By going through transmission and reception described above, the very-small bubbles in the observation area are collapsed and vanished. It is then considered that resetting is done, and transmission is responsively stopped only for the time interval different from that for the last time. Then, when any desired time that has been newly set comes, transmission and reception is carried out for a frame so as to derive the harmonics components.

(5) The above-described (3) and (4) are repeated with various intermittent time intervals to collect frame information of varying transmission-stop time intervals.

Here, in the present ultrasonic diagnostic apparatus, other than the above-described scan sequence, the scan sequence for shortening the TIC/MTT measurement time can be also executed. Thereabout, a description will be given below.

Next, in FIG. 3, region designation is made to a region of the ultrasonic image displayed on the display section 21 for assessment by the TIC measurement or the MTT measurement (in the below, referred to as "assessment area")(step S2). This designation is carried out responding to inputs coming from the mouse 13, the track ball 14, and others in the operation panel 15.

Next, with respect to the data (RF data in the first embodiment) corresponding to the assessment area of the echo signal collected for every ultrasonic image through scanning in step S2, the TIC/MTT measurement section 25 calculates a representative value of the concentration (intensity value). By plotting the resulting representative value on the coordinate plane in which the vertical axis denotes concentration, and the lateral axis denotes the intermittent transmission time, derived is such a TIC as shown in the middle part of FIG. 4, for example (step S3). The resulting TIC is displayed on the display section 21 via the memory synthesis section 11. In this step, the TIC measurement process in S3 is executed based on the echo signals not yet subjected to logarithmic compression by the logarithmic transformation unit 30B. Further, steps S2 and S3 may be executed at the same time.

Note here that the contrast agent generally varies in signal value depending on the administration concentration, dosage, dosing speed, or due to varying tissue characteristics on an individual basis, or due to the capability difference among the ultrasonic diagnostic apparatuses. Thus, there is no point in the absolute values of the signal values found in the TIC. Generally used for assessment are the values relative to the reference values, parameters exemplified by time-varying intensity, and the like.

In the present embodiment, the TIC/MTT measurement section 25 goes through the TIC measurement process based on the RF data. In addition thereto, in each embodiment that will be described later, in this step S3, the TIC/MTT measurement section 25 applies the process to each data including: IQ data (data having been subjected to phase detection by the receiver section 7 but not yet subjected to the process by the B-mode unit 30 or the CFM unit); B-mode detection data (data having been subjected to envelop detection by the envelop detection circuit 30A but not yet subjected to logarithmic transformation by the logarithmic transformation unit 30B); B-mode raster data (data having been subjected to envelop detection and logarithmic transformation by the B-mode unit 30 but not yet subjected to orthogonal transformation by the DSC section 8); and B-mode orthogonal transformation data (data having been subjected to orthogonal coordinate transformation by the B-mode DSC section 8).

Next, the TIC/MTT measurement section 25 goes through MTT measurement based on the TIC (step S4). Using the standardized TIC standardized by the saturation value (maximum concentration value) in the TIC shown in the lower part of FIG. 4 will lead to MTT. To be specific, in the standardized TIC of FIG. 4, MTT is derived by the area of area S (the diagonally shaded area shown in the standardized TIC of FIG. 4. In the below, referred to as "MTT area".) enclosed by the administration starting time of the contrast agent, the maximum value 1 at the time before reaching the saturation value, and the standardized TIC. The MTT area may be, structurally, automatically device-designated by the CPU 20 based on information about the TIC, or may be set by an operator using a manual through the mouse 13, the track ball 14, and others in the operation panel 15.

Herein, the unit of the MTT thus derived by the normalized TIC of FIG. 4 is a second. This MTT can be calculated not only from the normalized TIC but also from the non-normalized TIC found in the middle part of FIG. 4. That is, in the TIC in the middle part of FIG. 4, calculation may be done by normalizing, by a saturation value, an area derived for the area enclosed by the maximum value and the TIC in the range from the rising time of the TIC (the time when signal detection from the contrast agent is started) to the time reaching the saturation value.

Moreover, in the TIC/MTT measurement section 25, not only the TIC/MTT measurement, the bioinformation exemplarily shown below can be also measured.

Figure 5:
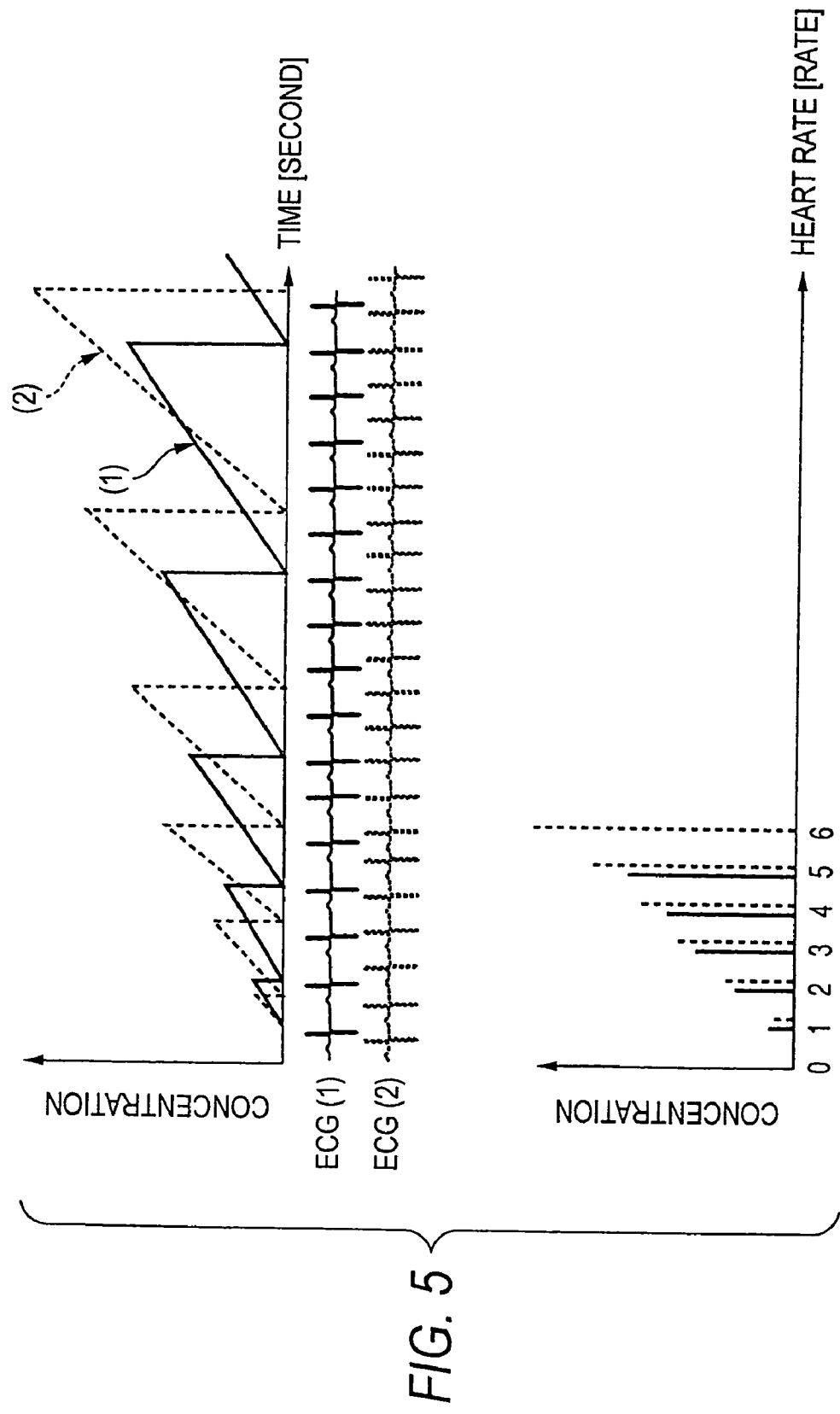
FIG. 5 is a conceptual diagram showing bioinformation MTB (Mean Transit Beat) measurable by a TIC/MTT measurement section 25.

The graph found in the lower part of FIG. 5 shows bioinformation MTB (Mean Transit Beat) measurable by the TIC/MTT measurement section 25. In the MTB, the vertical axis denotes the concentration, and the lateral axis denotes the heart rate. To measure such MTB, in steps S1 and S2 of FIG. 4, executed is the process similar to the case of MTT measurement, that is, the flash echo in which the transmission interval is synchronized with the ECG 1 (refer to the graph found in the upper part of FIG. 5). Then, in step S3, based on the signal measured by the ECG 1, the representative value derived for every image may be plotted onto the coordinate plane in which the vertical axis denotes the concentration, and the lateral axis denotes the heart rate. This MTB is the bioinformation to be generated by parameters being individually unique but not the absolute time, exemplified by assessment of cardiac temporal phase (e.g., the last period of contraction, the last period of expansion), normalization by the heart rate, and the like. Accordingly, using such an MTB expectably leads to effects of removing the susceptibility caused by varying heart rate for every individual due to each different age and body shape.

As described in the foregoing, in the TIC/MTT measurement process executed by the TIC/MTT measurement section 25, used are signals before compression by logarithmic transformation. Accordingly, TIC/MTT measurement can be carried out with accuracy thanks to abundant information, without suffering from the effects of less data information volume reduced due to logarithmic compression.

Furthermore, as shown in FIG. 4, the TIC based on signals before logarithmic compression will be ideally more linear. Thus, it is possible to carry out a fitting process more easily than the conventional case.

(Compensation Function)

Described next is the enhancement function of the present ultrasonic diagnostic apparatus in the TIC/MTT measurement.

The present ultrasonic diagnostic apparatus has a function of compensating any effects to the MTT caused by beam form, especially the effects to the MTT caused by beam difference in the depth direction. With this function, the TIC/MTT measurement can be carried out with higher reliability.

Figure 6A:
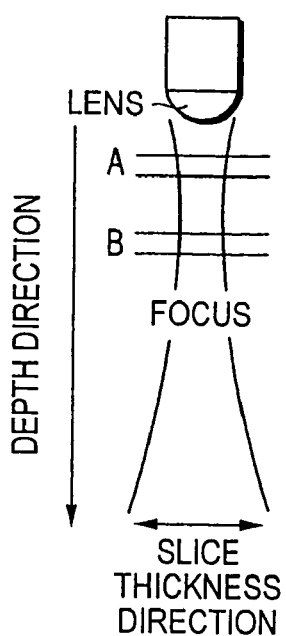
FIGS. 6A, 6B, and 6C are all a conceptual diagram for illustrating a compensation process to be executed with respect to the resultantly-derived MTT.
Figure 6C:
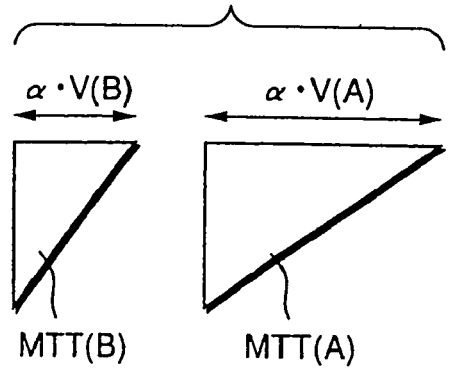
Figure 6B:
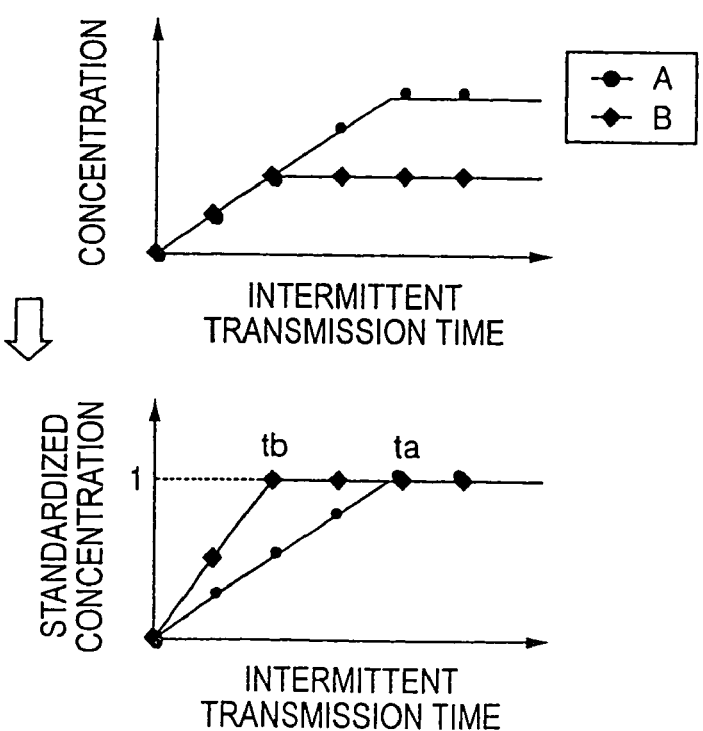

FIGS. 6A, 6B, and 6C are all a diagram for illustrating the compensation process to be executed to the resulting MTT. As shown in FIG. 6AA, the shape of the ultrasonic beam coming from the prove 4 is not constant, and varies depending on the depth. For example, in a one-dimensional array probe, focus adjustment is done in the slice-thickness direction by a lens, and thus the beam thickness varies depending on the depth. Accordingly, as shown in FIG. 6B, even if the contrast agent is uniformly distributed, a difference is observed between the TIC as a result of measurement based on the echo signal coming from a region A of a subject (in the below, referred to as A-TIC) and the TIC as a result of measurement based on the echo signal coming from a region B thereof (in the below, referred to as B-TIC).

In view thereof, in the present ultrasonic diagnostic apparatus, compensation is applied to the MTT in such a manner as to adjust the shape of the beam irradiated from the ultrasonic probe 4 depending on the depth. For example, when the region B being the focus point is used as a reference, as shown in FIG. 6C, variation of the MTTs caused by the acoustic fields varying depending on the depth is compensated by multiplying the MTT derived by the A-TIC (in the below, MTTA) by the sample volume of the acoustic field having the sound pressure capable of collapsing and vanishing the very-small bubbles or higher. In more detail, assuming that the sample volume of the acoustic field capable of collapsing and vanishing the very-small bubbles in the referential region B is VB, and the sample volume of the acoustic field capable of collapsing and vanishing the very-small bubbles in the compensating region A is VA, VB/VA is integrated into the MTT value derived in the region A. In this manner, variation of the MTTs caused by the beam shape can be compensated. Such a compensation process is executed by the CPU 20 reading a compensation coefficient corresponding to the transmission requirement from the storage section 27 to multiply the MTT thereby.

As such, by applying compensation to the MTT in such a manner as to adjust the shape of the beam irradiated from the ultrasonic probe 4 depending on the depth, the MTTs can be prevented from varying, favorably leading to the better accuracy of quantitative assessment.

In a preferable structure, if an operator designates an assessment area that has been firstly selected, using the designated position as a reference, an area of almost spatially equal to the sound pressure with which the very-small bubbles can be collapsed and vanished is displayed on an image as shown in FIG. 7. Then, MTT assessment is allowed only to the area. If this is the case, although limitation is imposed on the assessment area, it becomes possible to avoid the operator's erroneous assessment. Here, the frame data used for area selection is applied to the one derived when the contrast agent is fully filled in the scanning cross section.

(Scan Sequence for Shortening TIC/MTT Measurement Time)

Described next is the scan sequence realized by the present ultrasonic apparatus for shortening the TIC/MTT measurement time. This scan sequence is realized by the CPU 20 controlling the ultrasound transmission system (trigger generator 19, timing signal generator 18, and ultrasound transmission section 6) in accordance with a preset program.

Generally, if he blood flowing into the target tissue flows out after passing through the blood vessel system such as capillary tubes in the tissue in a controlled flow, the temporal change of the signal strength ideally shows a linear increase at where the TIC rises, and becomes constant in value when the volume of the contrast agent is saturated by the blood (refer to the lower part of FIG. 4 as an example).

Paying attention to this point, the present sequence performs MTT calculation by deriving the saturation value, the initial value, and the gradient of the rising part of the TIC to obtain the rising time, and the time of reaching the saturation value. Accordingly, without obtaining any sample point covering all, TIC/MTT creation is done from the rising part of the TIC. Thus, this successfully shortens the time taken for data collection.

Figure 8:
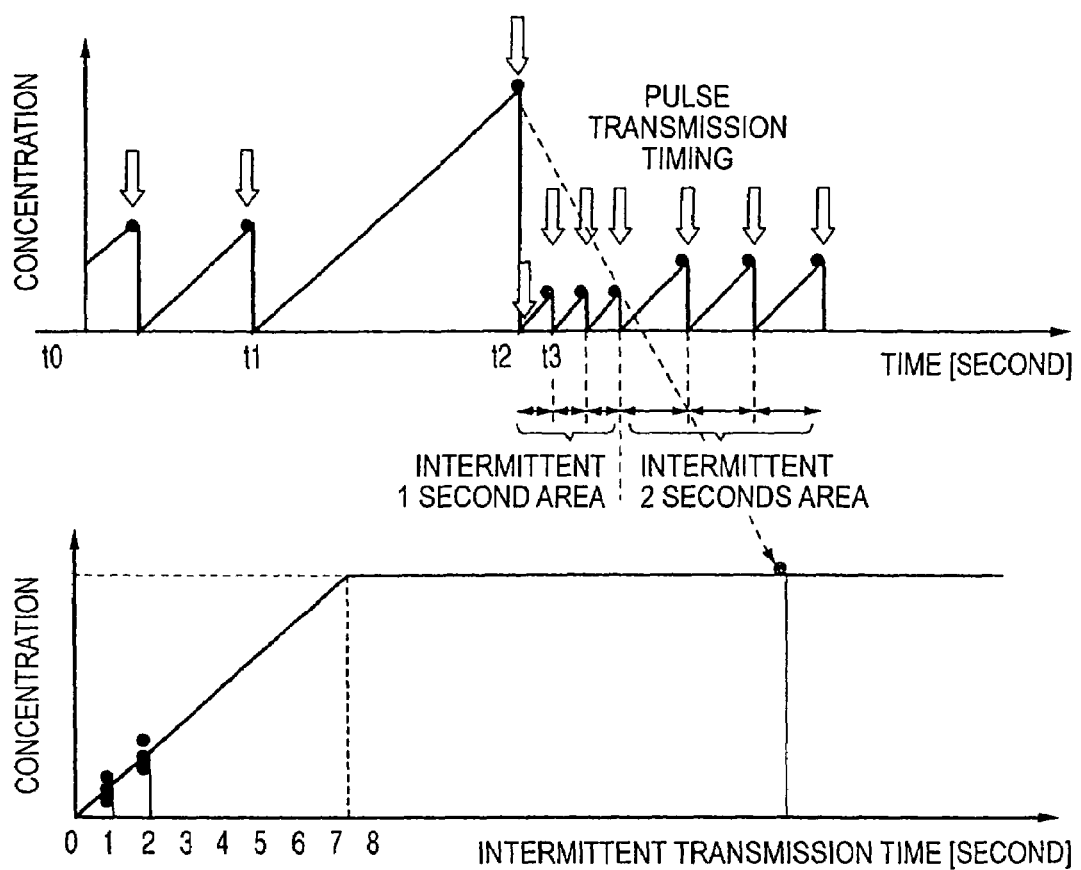
FIG. 8 is a conceptual diagram for illustrating the scan sequence to be executed by the present ultrasonic diagnostic apparatus, and the TIC as a result of measurement based on echo signals derived by the scan sequence.

FIG. 8 is a diagram for illustrating the scan sequence to be executed by the present ultrasonic diagnosis apparatus, and the TIC as a result of measurement based on the echo signal derived by the scan sequence.

In the graph found in the upper part of FIG. 8, the vertical axis denotes the strength of sound pressure, the lateral axis denotes the time, and arrows each indicate cross section scanning. In the same graph, a time range from t0 to t1 indicates the general scan sequence of continuous transmission such as B mode and color mode, and the time t1 and onward indicates the present scan sequence of intermittent transmission for TIC/MTT analysis. Here, the general scan sequence means the scan sequence for general imaging, the scan sequence for vanishing, collapsing, and refreshing the contrast agent in the scanning cross section, or the like.

To make the following description more specific, in the graph at the upper part of FIG. 8, with the assumption that the contrast agent is saturated in 20 [seconds], created from the time t1 and onward is the TIC covering 20 [seconds]. Note that, under the conventional technique, if TIC creation is done by such a sampling time as increasing by 1 [second], the very-small bubbles being the contrast agent may vanish and collapse for every scanning, resultantly requiring resetting. Thus, it takes 1+2+3+. . . +20=210 [seconds] in total.

In the graph at the upper part of FIG. 8, first the contrast agent for ultrasound is injected. Injection of this contrast agent is started at time t1. Alternatively, the contrast agent may be continuously injected into a vein before time t1 to complete injection at time t1 with gentle injection into blood on a measured amount basis. After time t1, wait until the very-small bubbles fully fill the scanning cross section (in this case, until time t2. The time interval between the times t1 and t2 is at least 10 seconds or longer but 30 seconds or shorter, preferably). During this time, there is no need to perform ultrasound transmission. However, monitoring scanning at low sound pressure not to collapse and vanish the very-small bubbles is a possibility to observe how filling of the very-small bubbles is done in real time, or to control any displacement of the cross section.

Thereafter, at time t2 when filling of the very-small bubbles is fully completed, scanning is done at high sound pressure being the intermittent transmission for the first imaging. In more detail, the very-small bubbles in the scanning cross section are collapsed and vanished to collect the frame data relating to the saturation value. Thus collected frame data includes both the harmonic components by very-small bubbles collapsing and vanishing, and the harmonic components from the soft tissues in the living body. And the absolute addition values thereof are stored in the frame memory 12. Herein, this scanning may be numerous-cross-section scanning (multishot scanning) for ensuring the very-small bubbles to completely collapse and vanish.

Thereafter, at time t3 that is a second after time t2 (before the very-small bubbles perfuse again), performed are scanning and data collection for signal collection only from the soft tissues of the living body. The frame data at this time t3 will be the initial value in the TIC. In view of avoiding variation of data values, in an alternative structure, scanning may be performed for a plurality of times at the same intermittent transmission intervals to adopt the average value thereof.

After time t3, intermittent transmission is automatically started in accordance with the intermittent transmission sequence that has been set in advance. In the intermittent transmission at this time, intermittent transmission with short time intervals is carried out at at least two or more different time intervals. At this time, if allowed to select two or more of intermittent transmissions in order from those having the shortest time intervals, the measurement time can be favorably shortened. In view of such circumstances, in the present embodiment, as shown in FIG. 8, executed are the intermittent transmission after time t2 at a second interval, and the scan sequence at two seconds interval.

Here, as to the intermittent transmission to be carried out in order from those having the shortest time intervals, it is preferable to carry out pulse transmission for a plurality of times with the same time intervals. By increasing the sample number, the variation of data can be suppressed, and the accuracy can be increased.

The TIC/MTT measurement section 25 derives the time of reaching the saturation time from the rising time of a point TIC intersecting at the initial value, the saturation value, and the straight line being the slope in the specifically-derived intermittent time. Based thereon, TIC creation is performed to calculate the area corresponding to the MTT. At this time, such TIC creation based on the rising part of the TIC can be applied with linear approximation. This is surely not restrictive, and an approximation method in consideration of system characteristics can be applied. For example, a possibility may be generally-known higher-order function approximation, spline approximation, or exponential function approximation.

In accordance with the present scan sequence, assuming that ultrasound transmission is carried out once 20 seconds after injection of the contrast agent, and then intermittent transmission is carried out for three times each at one [second] intervals and two [seconds] intervals. If this is the case, scanning can be done by 20+(1+2)×3=29 [seconds]. As such, the MTT can be derived by going through the short-time scanning, thereby reducing the temporal load imposed on patients and operators.

Herein, to shift into the scan sequence, it is preferable for the operator to first check by monitoring scanning whether the contrast agent is filled over the scanning cross section, and if so, he or she activates the operation panel switch at any desired timing. In an alternative manner, in accordance with a preset program, the scan sequence is preferably started for MTT analysis automatically at any predetermined time. Such automatic shifting is not restrictive, and in an alternative structure, the operator's manual operation will do. If this is the case, to allow the operator to actively control shifting from the initial state to monitoring scanning, and initial collection of saturation value data, considered is such a structure that depressing switches of the operation panel will start such an operation.

Further, in the present scan sequence, it is possible to observe the dynamic behaviors of the contrast agent in real time by performing low sound pressure scanning, i.e., monitoring scanning, not to collapse and vanish the very-small bubbles between times t1 and t2 in FIG. 8 as already described.

Figure 9:
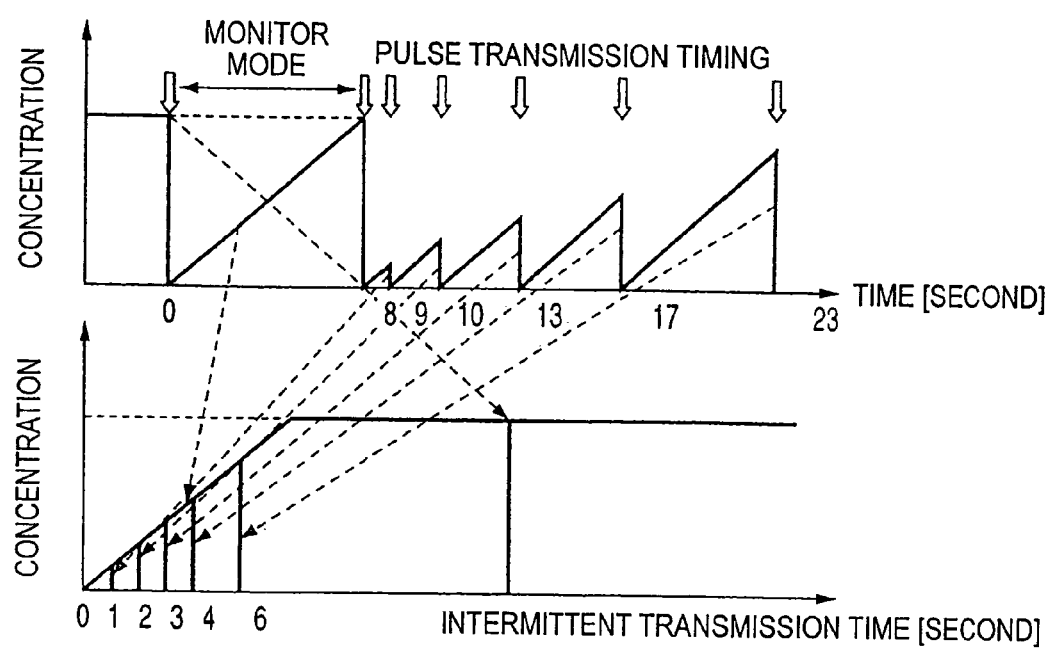
FIG. 9 is a conceptual diagram for illustrating the TIC/MTT measurement utilizing a monitoring mode.

FIG. 9 is a diagram for illustrating the TIC/MTT 15 measurement utilizing the monitoring mode (Monitor Mode). As shown in the upper part of FIG. 9, monitoring scanning is performed from time t1 to t2. Alternatively, the resulting frame data may be previously stored in a storage medium such as memory to perform TIC analysis. Or, simultaneous display is a possibility with the TIC derived by gradually changing the intermittent transmission intervals. In this case, if the signal strength scale along the vertical axis is not the same, this increases the difficulty of comparative study. Thus, there needs to first normalize both by using the respective saturation values to perform display with the same scale.

The TIC based on this monitoring scanning is low in S/N. The issue here is that, presumably, the result derived by normalizing the TIC by the saturation value, and the result derived by normalizing the TIC, by the saturation value, as a result of gradually-changed intermittent transmission intervals ideally show each similar behaviors, and render each similar curves. There may be a case, however, that the very-small bubbles may collapse and vanish at the time of monitoring depending on the acoustic fields, the concentration of the contrast agent, and the type of the contrast agent. In such a case, their rising parts have each different gradient, thus a possible application thereof is an index for sound pressure control at the time of monitoring.

In accordance with the present sequence, in the MTT analysis using the contrast agent for ultrasound, it is possible to improve the accuracy and reliability, and to shorten the examination time. As a result, assessment can be carried out in an effective and efficient manner, and the load to be imposed on patients and operators can be reduced, thereby leading to throughput increase.

(Effective Information Extraction Function)

Described next is the effective information extraction function provided to the ultrasonic diagnostic apparatus 100 of the present embodiment. The present ultrasonic diagnostic apparatus 100 performs TIC/MTT measurement with respect to echo signals extracted by this function. Here, this effective information extraction function is disclosed in detail in JP-A-2000-013563.

Generally, even if it is difficult to collapse and vanish the very-small bubbles locating in the cross section by one-time scanning, utilizing multishot performing scanning for various frames will vanish most of the very-small bubbles in the scanning cross section in an effective manner. This means that using information about every frame data as a result of multishot will lead to information about almost all of the very-small bubbles found in the cross section within the time of multishot.

Accordingly, it is possible to extract only information about any effective contrast agent to derive as a piece of frame data in the following manner. That is, the information about frame data derived by multishot is added for every coordinates, integration information relating to the contrast agent and the second harmonic components from the soft tissues of the living body, and then using the last frame data of multishot, the accumulated value of the second harmonic components from the soft tissues of the living body is deducted. This is the effective information extraction process, and in the present embodiment, the process is executed as follows based on the RF data for every frame.

Figure 10:
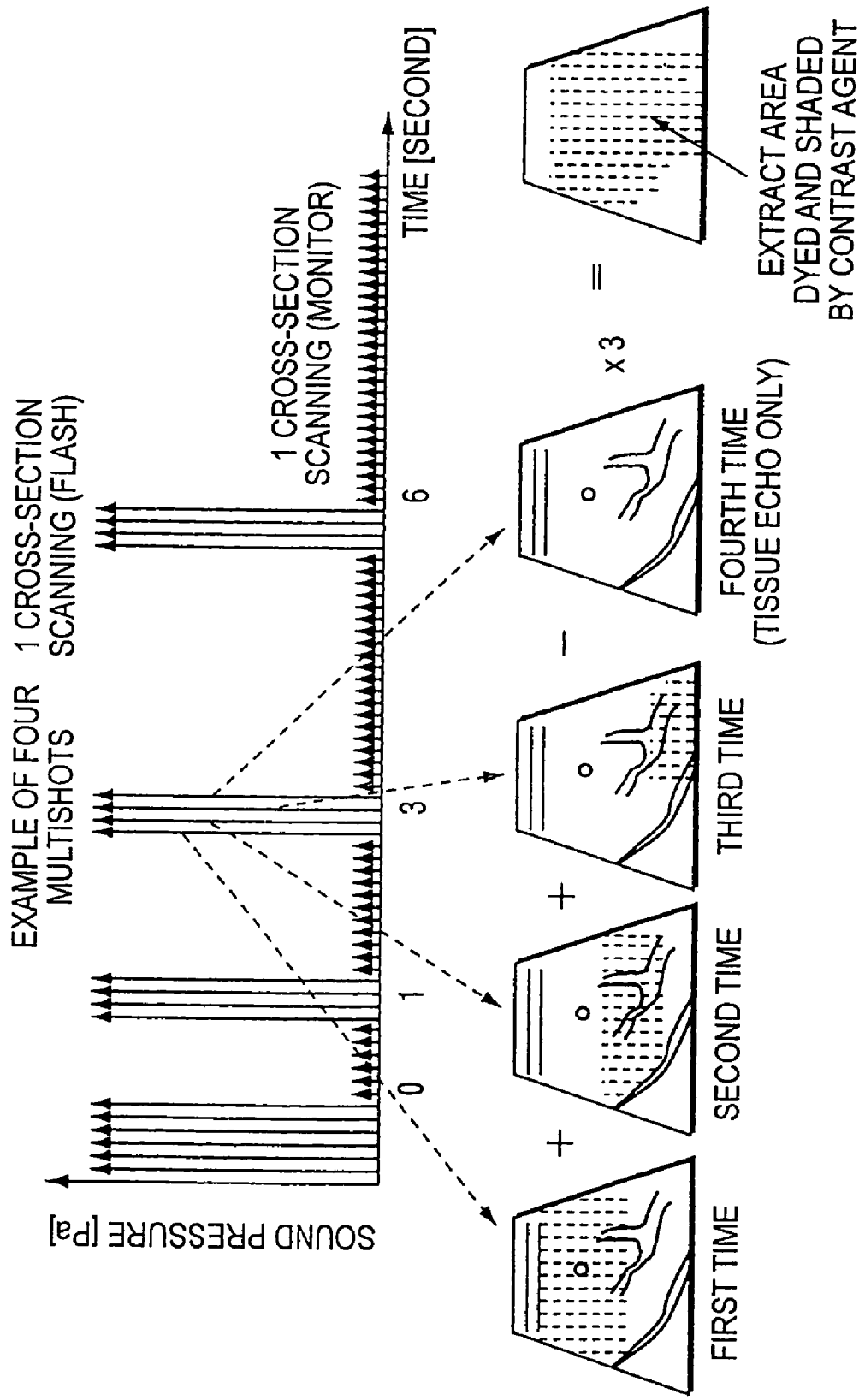
FIG. 10 is a conceptual diagram for illustrating the effective information extraction process.

FIG. 10 is a conceptual diagram for illustrating such an effective information extraction process. As shown in the upper part of FIG. 10, assuming that the multishot number is 4, and the ith frame data of the nth multishot in the intermittent transmission is F(n, i) (in this example, i takes values of i=1, 2, 3, and 4), the frame data Fn having been subjected to the nth effective information extraction process in the intermittent transmission is denoted by $$Fn = F(n, 1) + F(n, 2) + F(n, 3) - F(n, 4) \times 3 \qquad (1)$$

Or, through expansion, denoted as $$Fn = ps[F(n, 1) - F(n, 4)] + ps[F(n,2) - F(n, 4)] + ps[F(n, 3) - F(n,4)] \qquad (2)$$

Herein, the function ps[ ] executes the process that is previously operator-designated or device-designated. For example, if ps[ ] is provided with the parenthesized process in the mathematical calculation, the result will be equivalent to the equation (1).

When shadowing occurs, Fn may be a negative value in the equation (1) because tissue harmonics are deducted from the no-signal section. Therefore, because the signal strength is originally increased by the contrast agent, this may impair quantitativity if the value is turned into positive. In such a case, preferably, the equation (2) is used to execute the process in which ps[ ] replaces any value equal to or smaller than a threshold value (e.g., 0) with 0.

As another technique, first a difference is taken between any two frames, any value equal to or smaller than a certain threshold value (e.g., 0) is replaced with 0 in a similar manner to the above, and then such a statistic value as average or standard deviation value is calculated. Utilizing such statistical values, any area in which the very-small bubbles are vanished and collapsed enough to be assessed is designated as an assessable area by drawing a box therearound or by coloring the same (opaque or transparent) to increase the reliability of the assessment value. For example, any area with a value having 70 percent of the average value is regarded as the assessable area. Herein, such a numerical value as indicating percentage should be appropriately determined empirically. Also, a determination is made whether thus designated assessment target ROI is locating in the assessable area while being included in the frame data derived by every intermittent transmission being the assessment target. Only if determined as being in the assessable area, the quantitative assessment is carried out. Alternatively, displayed may be a region previously multiplied over the frame data derived by every intermittent transmission being the assessment target.

During the scanning performed to derive the TIC, the scanning cross section may be displaced due to the operator's unsteady hand(s) and the subject's body movement (breathing included). Thus, an editing function is preferably included for frame data selection.

By going through the above process, derived is an RF data cluster on a frame basis as a result of effective extraction of information about the very-small bubbles in any target scanning cross section. Based on the RF data cluster for every frame, the CPU 20 calculates the representative value in the assessment area set by the operator, for example, and executes the TIC/MTT measurement while controlling the TIC/MTT measurement section 25.

According to the above structure, even if the injection volume of the contrast agent is high or the concentration thereof is high, detection of blood flow perfusion, and the quantitative assessment of the perfusion can be carried out easily and effectively using the RF data not yet subjected to a compression process. (Second Embodiment)

In a second embodiment, shown is an ultrasonic diagnostic apparatus 102 for executing a TIC/MTT measurement process based on IQ data (data having been subjected to phase detection by the receiver section 7 but not yet subjected to the process by the B-mode unit 30 or the CFM unit).

Figure 11:
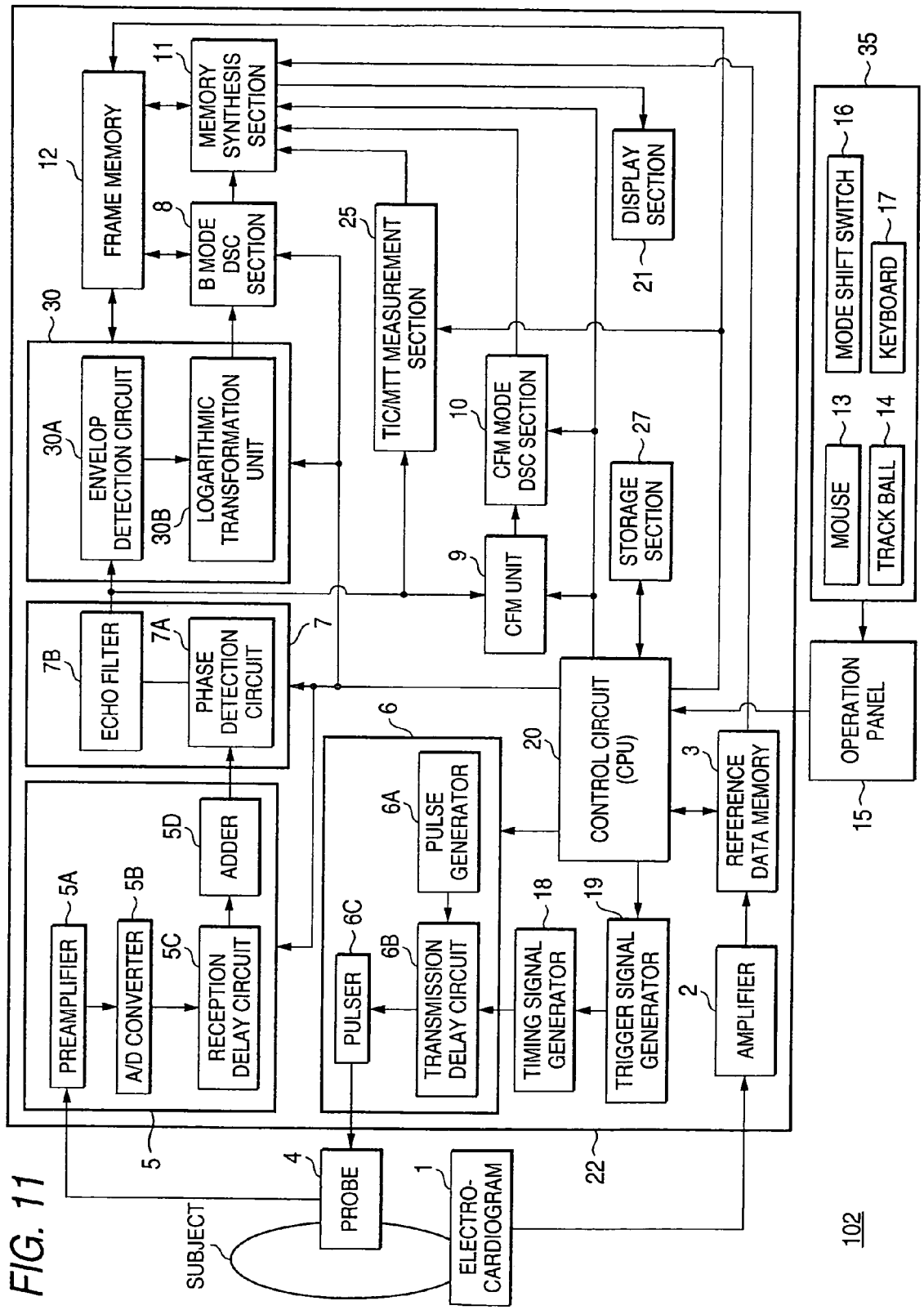
FIG. 11 is a block diagram showing the structure of the ultrasonic diagnostic apparatus 100 according to a second embodiment.

FIG. 11 is a block diagram showing the structure of the ultrasonic diagnostic apparatus 102 of the present embodiment. In FIG. 11, the TIC/MTT measurement section 25 receives the IQ data having been subjected to phase detection from the receiver section 7 to go through the TIC/MTT measurement process. This TIC/MTT measurement process is similar to the first embodiment. As to the effective information extraction process utilizing the IQ data, it is possible to execute that in a similar manner to the first embodiment.

With such a structure, the effects similar to the first embodiment can be achieved. In the second embodiment, due to high-speed calculation and hardware limitation, the IQ data may be shorter in data length compared with the RF data (carry less information). If this is the case, it is possible to reduce the calculation load. Further, by using the receiver section 7, any desired frequency components can be advantageously extracted.

(Third Embodiment)

A third embodiment shows an exemplary TIC/MTT measurement process to be executed based on B-mode detection data (data having been subjected to envelop detection by the envelop detection circuit 30A but not yet subjected to logarithmic transformation by the logarithmic transformation unit 30B).

Figure 12:
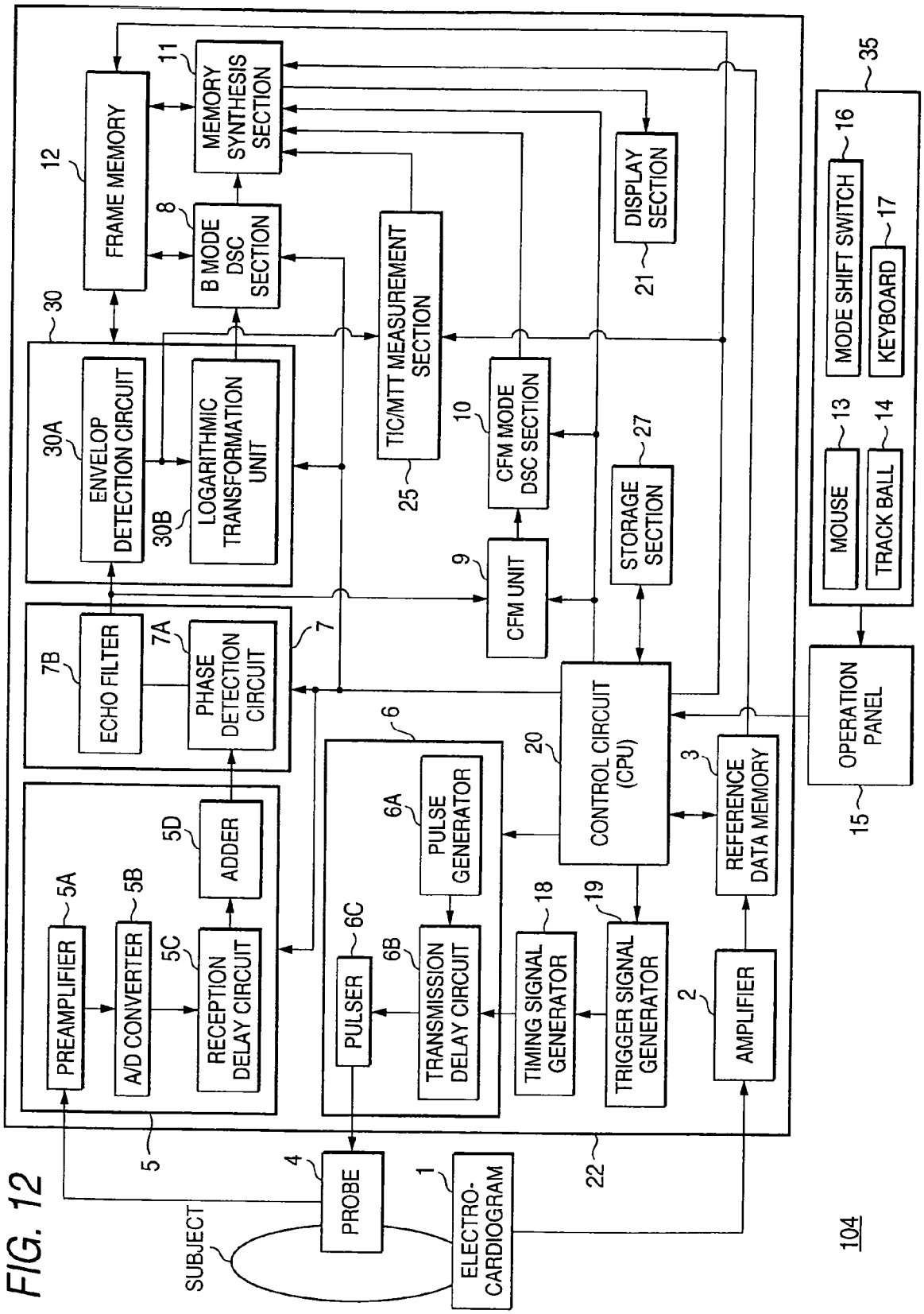
FIG. 12 is a block diagram showing the structure of an ultrasonic diagnostic apparatus 104 according to a third embodiment.

FIG. 12 is a block diagram showing the structure of an ultrasonic diagnostic apparatus 104 of the present embodiment. In FIG. 12, the TIC/MTT measurement section 25 receives, from the B-mode unit 30, the B-mode detection data having been subjected to envelop detection by the envelop detection circuit 30A to go through the TIC/MTT measurement process. This TIC/MTT measurement process is similar to the first embodiment. As to the effective information extraction process utilizing the B-mode detection data, it is possible to execute in a similar manner to the first embodiment.

With such a structure, the effects similar to the first embodiment can be achieved.

Actually, the B-mode detection data is amplitude information without phase information. Thus, the data length thereof is much shorter than the RF data, and thus the calculation load is reduced in a practical sense. Further, it is not having been subjected to data compression by the logarithmic transformation unit 30B, thus no information reduction occurs due to the compression process.

(Fourth Embodiment)

A fourth embodiment shows an exemplary TIC/MTT measurement process to be executed based on B-mode raster data (data having been subjected to envelop detection and logarithmic transformation by the B-mode unit 30 but not yet subjected to orthogonal transformation by the DSC section 8). Specifically, in the first to third embodiments, the TIC/MTT measurement is carried out based on echo signals not yet subjected to logarithmic transformation (i.e., before compression). In the second embodiment, shown is an exemplary TIC/MTT process to be executed by extracting intensity information before logarithmic transformation again through antilogarithmic transformation applied to detection signals having gone through the process in the receiver section 7.

Figure 13:
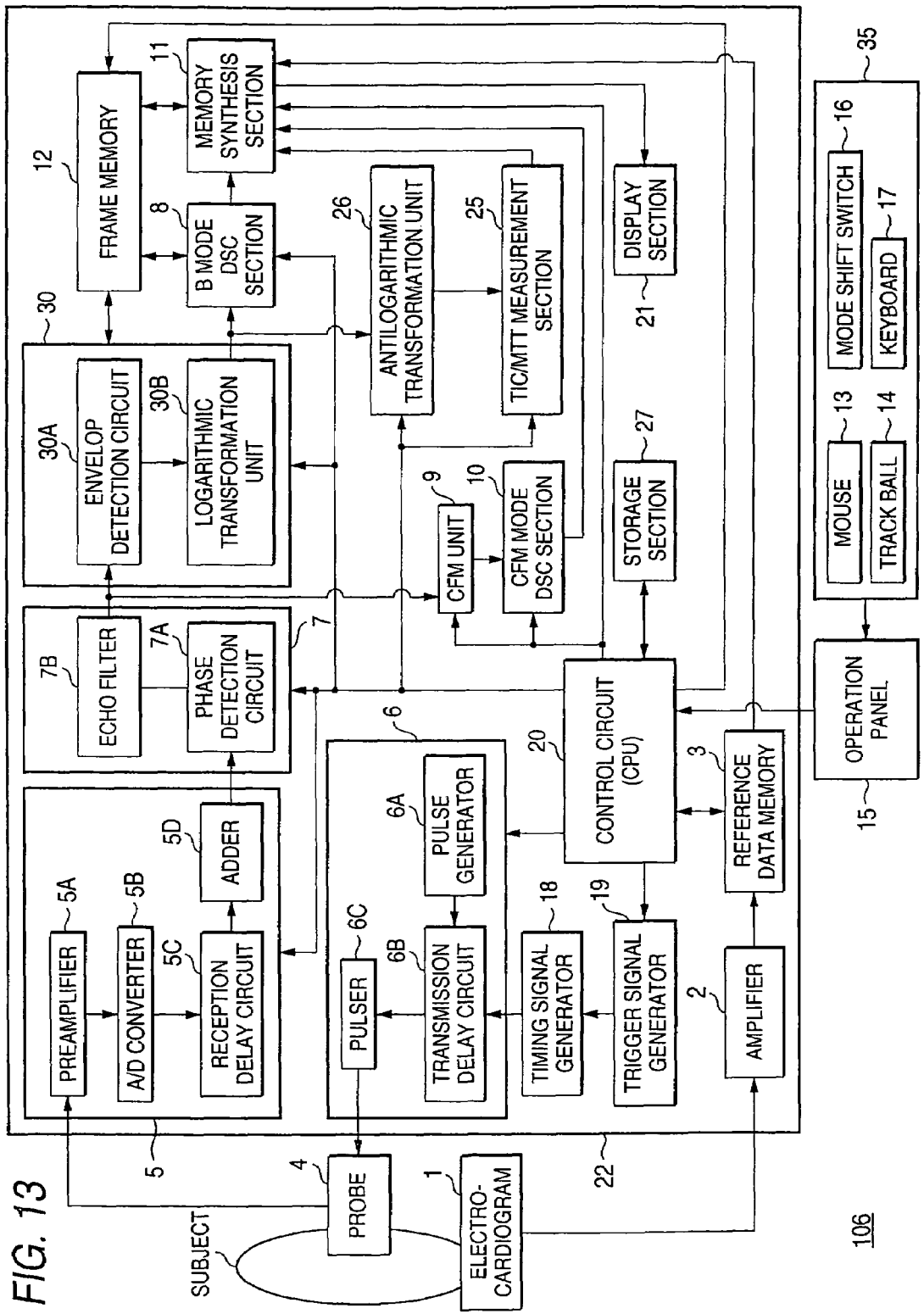
FIG. 13 is a block diagram showing the structure of an ultrasonic diagnostic apparatus 106 according to a fourth embodiment.

FIG. 13 is a block diagram showing the structure of an ultrasonic diagnostic apparatus 106 of the present embodiment. As shown in FIG. 13, the ultrasonic diagnostic apparatus 106 further includes an antilogarithmic transformation unit 26. This antilogarithmic transformation unit 26 receives, from the B-mode unit 30, B-mode raster data having been subjected to logarithmic transformation to perform antilogarithmic transformation. The data as a result of decoding by antilogarithmic transformation and being put back to the echo signal having the linear signal strength is output to the TIC/MTT measurement section 25. The TIC/MTT measurement section 25 goes through the TIC/MTT measurement based on thus input echo signal.

The TIC/MTT measurement section 25 goes through the TIC/MTT measurement in a similar manner to the first embodiment based on the data having been subjected to antilogarithmic transformation.

The effective information extraction process utilizing the B-mode raster data after logarithmic transformation is as follows. That is, the antilogarithmic transformation unit 26 receives the B-mode raster data from the B-mode unit 30 responding to any predetermined operation to carry out antilogarithmic transformation. The echo signal as a result of decoding by antilogarithmic transformation executed by the antilogarithmic transformation unit 26 is output to the TIC/MTT measurement section 25. Based on thus received echo signal, the TIC/MTT measurement section 25 calculates the representative value (e.g., average value) in the assessment area designated by the operator, and then based on the respective representative values, the TIC/MTT measurement is carried out.

With such a structure, the effects similar to the first embodiment can be achieved. Even if the first to third embodiments are difficult due to hardware limitation, and thus if the B-mode raster data having been subjected to logarithmic transformation and compression is used, linear fitting becomes possible at the TIC rising parts under the condition that the antilogarithmic transformation unit 26 applies data conversion thereto into linear. Accordingly, this eases regression calculation.

(Fifth Embodiment)

A fifth embodiment shows an exemplary TIC/MTT measurement process to be executed based on B-mode orthogonal transformation data (data having been subjected to orthogonal coordinate transformation by the B-mode DSC section 8).

Figure 14:
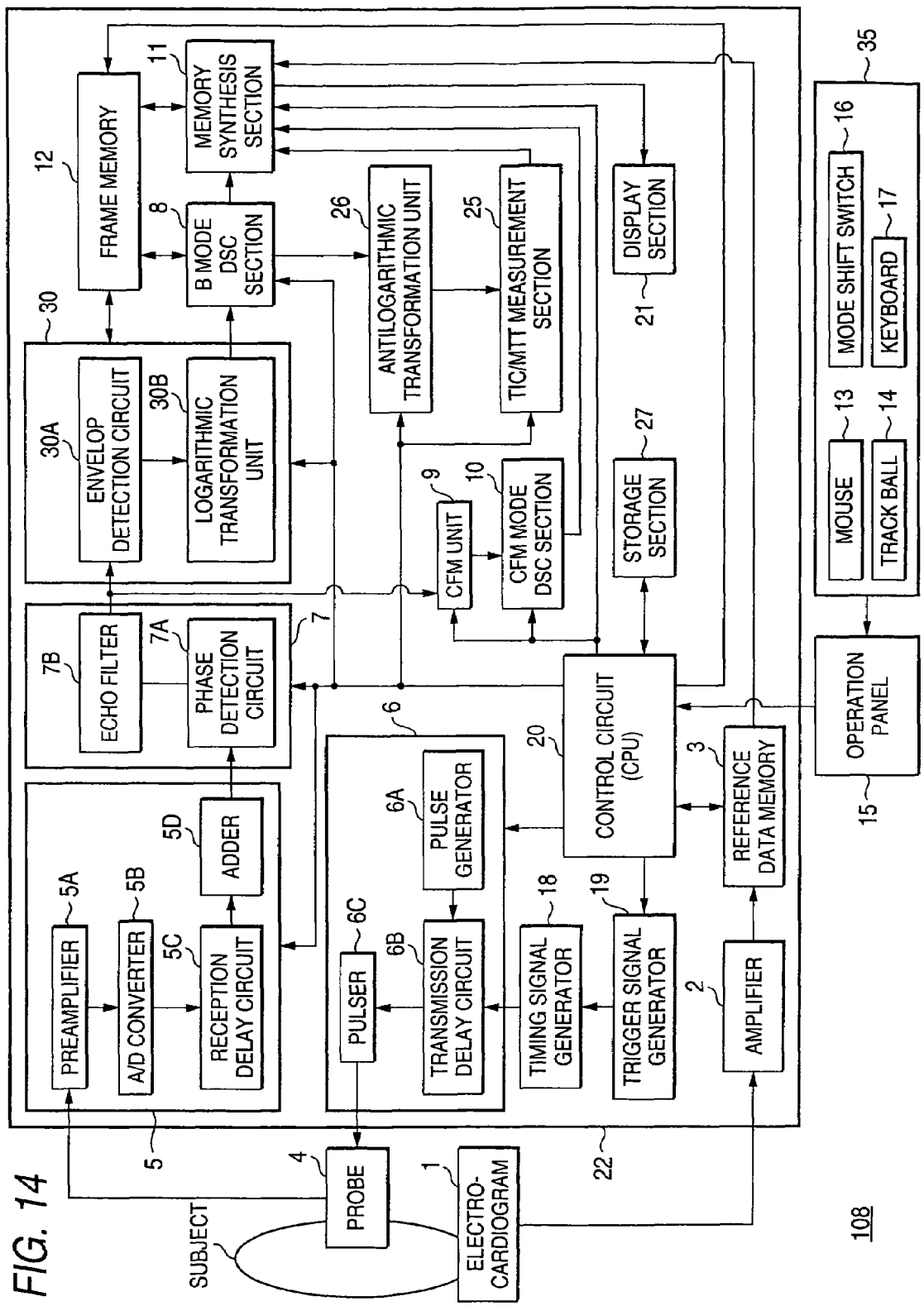
FIG. 14 is a block diagram showing the structure of an ultrasonic diagnostic apparatus 108 according to a fifth embodiment.

FIG. 14 is a block diagram showing the structure of an ultrasonic diagnostic apparatus 108 of the present embodiment. As shown in FIG. 14, the antilogarithmic transformation unit 26 receives, from the B-mode DSC section 8, B-mode orthogonal conversion data to perform antilogarithmic transformation. The echo signal having been put back to the linear signal strength by antilogarithmic transformation by the antilogarithmic transformation unit 26 is output to the TIC/MTT measurement section 25. The TIC/MTT measurement section 25 goes through the TIC/MTT measurement based on thus received echo signal. This TIC/MTT measurement process is similar to the first embodiment.

The effective information extraction process utilizing the B-mode orthogonal transformation data after logarithmic transformation is as follows. That is, the antilogarithmic transformation unit 26 receives the B-mode orthogonal transformation data from the B-mode DSC section 8 responding to any predetermined operation to carry out antilogarithmic transformation. The echo signal as a result of decoding by antilogarithmic transformation executed by the antilogarithmic transformation unit 26 is output to the TIC/MTT measurement section 25. Based on thus received echo signal, the TIC/MTT measurement section 25 calculates the representative value (e.g., average value) in the assessment area designated by the operator, and then based on the respective representative values, the TIC/MTT measurement is carried out.

With such a structure, the effects similar to the first embodiment can be achieved. Even if the first to third embodiments are difficult due to hardware limitation, and thus the B-mode raster data having been subjected to logarithmic transformation and compression is used, linear fitting becomes possible at the TIC rising parts under the condition that the antilogarithmic transformation unit 26 applies data conversion thereto into linear. Accordingly, this eases regression calculation.

Here, also in the ultrasonic diagnostic apparatuses according to the second to fifth embodiments described above, needless to say, the compensation function and the effective information extraction function described in the first embodiment can be both realized.

Although a plurality of ultrasonic diagnostic apparatuses are shown, in view of calculation accuracy, as to the TIC/MTT measurement process, it is preferable to use output signals coming from any unit provided in the previous stage as much as possible. This is because, as the unit is provided to further subsequent stage, the data information volume of the output signal becomes less.

As such, the present invention is described by referring to the embodiments, and those skilled in the art can conceive numerous variations and modifications within the scope of the present invention. Thus, those variations and modifications are understood as belonging to the scope of the present invention, and can be devised without departing from the scope thereof.

Moreover, the above embodiments include inventions at various stages, and numerous inventions can be derived through appropriate combinations of a plurality of disclosing components. For example, even if some components are deleted from all of those shown in the embodiments, the object mentioned in the section referring to the object to be solved by the invention can be successfully solved, and when at least one effect of those mentioned in the section referring to the effects of the invention is achieved, the structure from which the corresponding component is deleted is derived as an invention.

According to the present invention described above, realized is an ultrasonic diagnostic apparatus with which effects caused by the depth can be reduced, and MTTs can be derived with assured accuracy and with high reproducibility through short-time scanning.

What is claimed is:

1. An ultrasonic diagnostic apparatus, comprising:
   an ultrasonic probe for transmitting ultrasound to a subject having been injected with a contrast agent, and receiving ultrasonic echo from the subject;
   a driving signal generator for generating a driving signal for driving the ultrasonic probe;
   a control unit for controlling the driving signal generator based on a predetermined scan sequence for plotting a time-varying concentration graph of the contrast agent;
   a signal processor for applying a detection process and a logarithmic transformation process to the ultrasonic echo;
   an image generator for generating an ultrasonic image based on an output of the signal processor;
   an antilogarithmic transformation unit for applying an antilogarithmic transformation process to an output signal coming from at least either of the signal processor or the image generator; and
   a processor for plotting a time-varying graph based on the output signal coming from the antilogarithmic transformation unit.

2. The ultrasonic diagnostic apparatus according to claim 1, wherein
   the measurement processor derives a mean transit time of a blood flow based on the time-varying graph.

3. The ultrasonic diagnostic apparatus according to claim 1, wherein
   the control unit controls the driving signal generator in such a manner that an initial scanning is performed after a lapse of time in which the contrast agent is fully filled in a target part of the subject, and
   based on a result of the initial scanning, the measurement processor normalizes a value of the scanning performed after the initial scanning to plot the graph.

4. An ultrasonic diagnostic apparatus, comprising:
   an ultrasonic probe for transmitting ultrasound to a subject having been injected with a contrast agent, and receiving ultrasonic echo from the subject;
   a driving signal generator for generating a driving signal for driving the ultrasonic probe;
   a control unit for controlling the driving signal generator based on a predetermined scan sequence for plotting a time-varying concentration graph of the contrast agent;
   a signal generator for generating a first signal as a result of a detection process and a logarithmic transformation process applied with respect to the ultrasonic echo, and a second signal as a result of the detection process applied with respect to the ultrasonic echo;
   an image generator for generating an ultrasonic image based on the first signal; and
   a measurement processor for plotting the time-varying graph based on the second signal.

5. The ultrasonic diagnostic apparatus according to claim 4, wherein
   the measurement processor derives a mean transit time of a blood flow based on the time-varying graph.

6. The ultrasonic diagnostic apparatus according to claim 4, wherein
   based on a result of the scanning performed for an initial time after a lapse of time in which the contrast agent is fully filled in a target part of the subject, the measurement processor normalizes a value of the scanning performed after the initial scanning to plot the graph.

7. An ultrasonic diagnostic apparatus, comprising:
   an ultrasonic probe for transmitting ultrasound to a subject having been injected with a contrast agent, and receiving ultrasonic echo from the subject;
   a driving signal generator for generating a driving signal for driving the ultrasonic probe;
   a control unit for controlling the driving signal generator based on a predetermined scan sequence for deriving a time-varying concentration of the contrast agent;
   an image generator for generating an ultrasonic image based on the ultrasonic echo; and
   a measurement processor for plotting a time-varying concentration graph of the contrast agent based on the ultrasonic echo, and for compensating a mean transit time of a blood flow derived from the time-varying graph depending on a measurement position depth.

8. The ultrasonic diagnostic apparatus according to claim 7, wherein
   the control unit controls the driving signal generator in such a manner that an initial scanning is performed after a lapse of time in which the contrast agent is fully filled in a target part of the subject, and based on a result of the initial scanning, the measurement processor normalizes a value of the scanning performed after the initial scanning to plot the graph.

9. An ultrasonic diagnostic apparatus, comprising:
   an ultrasonic probe for transmitting ultrasound to a subject having been injected with a contrast agent, and receiving ultrasonic echo from the subject;
   a driving signal generator for generating a driving signal for driving the ultrasonic probe;
   a control unit for controlling the driving signal generator based on a predetermined scan sequence for plotting a time-varying concentration graph of the contrast agent;
   an image generator for generating an ultrasonic image based on the ultrasonic echo; and
   a measurement processor for plotting the time-varying concentration graph of the contrast agent based on the ultrasonic echo, and for compensating the time-varying graph depending on a measurement position depth.

10. The ultrasonic diagnostic apparatus according to claim 9, wherein
    the control unit controls the driving signal generator in such a manner that an initial scanning is performed after a lapse of time in which the contrast agent is fully filled in a target part of the subject, and based on a result of the initial scanning, the measurement processor normalizes a value of the scanning performed after the initial scanning to plot the graph.

* * * * *